US012622801B2

(12) United States Patent
Justin et al.

(10) Patent No.: US 12,622,801 B2
(45) Date of Patent: May 12, 2026

(54) ERECTILE FITNESS DEVICE

(71) Applicant: FirmTech, Inc., Bozeman, MT (US)

(72) Inventors: Elliot Justin, Bozeman, MT (US);
Jonathan Thai, San Jose, CA (US);
Michael Yim, San Jose, CA (US);
Blake Johnson, Hilo, HI (US); **Peter
Yoo, Santa Clara, CA (US); Siri
Sakulyong, Samutprakran (TH); Cesar
Viramontes**, Oakland, CA (US)

(73) Assignee: FirmTech, Inc., Bozeman, MT (US)

( * ) Notice: Subject to any disclaimer, the term of this
patent is extended or adjusted under 35
U.S.C. 154(b) by 1142 days.

(21) Appl. No.: 17/587,158

(22) Filed: Jan. 28, 2022

(65) Prior Publication Data

US 2023/0065494 A1     Mar. 2, 2023

(51) Int. Cl.
*A61F 5/41* (2006.01)

(52) U.S. Cl.
CPC .......... *A61F 5/41* (2013.01); *A61F 2005/414*
(2013.01)

(58) Field of Classification Search
CPC ................ A61F 5/41; A61F 2005/414; Y10T
24/44248; Y10T 24/44239; Y10T
24/1408; Y10T 24/141; Y10T 24/142;
Y10T 24/3416; Y10T 24/3916; Y10T
24/3929; Y10T 24/3987; Y10T 24/3991;
Y10T 24/44128; F16G 11/106
See application file for complete search history.

(56) References Cited

U.S. PATENT DOCUMENTS

| | | | |
|---|---|---|---|
| 4,569,108 A * | 2/1986 | Schwab | B62J 7/08 |
| | | | 24/17 AP |
| 5,370,130 A * | 12/1994 | Hess | A61F 6/04 |
| | | | 128/842 |
| 6,162,188 A | 12/2000 | Barnea | |
| 6,389,659 B1 * | 5/2002 | Jacobs | A63C 19/062 |
| | | | 116/173 |
| 6,543,094 B2 * | 4/2003 | D'Addario | H02G 3/26 |
| | | | 24/459 |
| 7,678,042 B2 | 3/2010 | Jackson | |
| 7,712,195 B1 * | 5/2010 | Selby | F16G 11/00 |
| | | | 24/301 |
| 9,247,904 B2 | 2/2016 | Hotaling | |

(Continued)

FOREIGN PATENT DOCUMENTS

| | | |
|---|---|---|
| DE | 202005007340 | 10/2005 |
| WO | 2003005940 | 1/2003 |

OTHER PUBLICATIONS

European Search Report for EP23153747, completed Jun. 12, 2023.

*Primary Examiner* — Samuel G Gilbert
(74) *Attorney, Agent, or Firm* — Wissing Miller LLP

(57) ABSTRACT

A device for enhancing the tumescence of an erection is
disclosed. The device has a body shaped to conform to the
dorsal surface of a wearer's penis. A latch is disposed on one
end of the body and a loop of elastic material extends from
the opposite end of the body. A wearer attaches the device
by stretching the loop from the body, placing the body
against his penis, inserting his testicles through the loop and
engaging the loop with the latch. One portion of the loop
encircles the shaft of the penis in front of the scrotum and a
second encircles the penis and scrotum behind the scrotum.
Elastic rebound of the loop applies compressive force to the
penis and scrotum, modifying blood flow in the penis and
increasing tumescence.

11 Claims, 8 Drawing Sheets

(56)         References Cited

U.S. PATENT DOCUMENTS

| | | | |
|---|---|---|---|
| 10,483,784 B2 | 11/2019 | Konik et al. | |
| 2009/0318755 A1 | 12/2009 | Adams et al. | |
| 2016/0108989 A1* | 4/2016 | Symons | B42D 3/10 |
| | | | 29/452 |

* cited by examiner

ERECTILE FITNESS DEVICE

BACKGROUND OF THE INVENTION

1. Field of the Invention

The present disclosure relates to a device worn around the penis and scrotum of a male human. More particularly, the present disclosure relates to an erection device that securely and adjustably fits around both the penis and scrotum of the human and that applies pressure to the shaft of the penis.

2. Description of the Related Art

Penis rings are devices designed to be worn by men during sexual activity. Such rings may apply pressure to portions of the penis to provide pleasurable sensations, to stimulate blood flow into the penis, and to increase blood pressure in the tissues of the penis causing greater tumescence. Penis rings may be formed from elastic materials so that when stretched over the penis, the elastic recoil of the ring applies pressure to the penis. This pressure may alter the flow of blood out of the tissues of the penis.

Penis rings may be formed from an elastic material and have an inner diameter smaller than the expected diameter of the erect penis. The user stretches the ring and slides it onto the shaft of his penis. The ring is positioned near the base of the penis to compress the venous outflow from the penis and testicles.

There are a number of problems with known penis rings. In some cases, the ring has a fixed minimum inside diameter when no stretching force is applied. Such a ring may fit too tightly or too loosely to the penis. For example, in a flaccid state, the penis may be inserted into the ring without a problem, but when the penis becomes erect, the force applied as the ring stretches around the penis may be too great, leading to discomfort. Once in place, the ring may be difficult to remove while the penis is still erect. In other cases, where the ring is too large, there may not be sufficient engagement between the penis and the ring when the penis is erect to hold the ring on the penis or to allow the ring to apply sufficient pressure to the penis. In order to accommodate users with different sized penises. a range of different rings may be required so that a ring with the correct inner diameter can be found Because the diameter of the penis changes significantly between the flaccid and the erect state, the ring may not be held securely on the penis until an erection is achieved. Should the strength of the erection fluctuate, the ring may become loose. This is especially problematic during sexual intercourse. Motion of the penis and contact with body parts of the wearer and the wearer's sexual partner can cause the ring to become dislodged or moved to a part of the penis that does not provide the desired pressure on the wearer's vasculature.

Known penis rings may also be uncomfortable to put on and take off. If the penis is erect when the ring is applied, it will need to be stretched over the penis and then moved along the shaft to the base of the penis. Moving a tight ring along the sensitive tissues of the penis may be uncomfortable. Likewise, removing the ring while the penis is erect requires the ring to slide along sensitive tissues.

Known penis rings may include extensions or other structures designed to contact parts of the body of the wearer or the wearer's sexual partner, such as the clitoris, labia, anus, etc. These structures are designed to provide stimulation for the wearer and/or the wearer's the sexual partner during intercourse. These structures may include vibrators or mechanical manipulators to apply vibration or motion to erogenous tissues. To reliably locate such structures in a position to contact the partner in the intended way, the radial position of the penis ring about the penis needs to be fixed. Where the degree of tumescence varies, the penis ring may become loose so that structures on the ring are no longer located where they can reliably contact the desired erogenous tissues.

BRIEF SUMMARY OF THE INVENTION

Embodiments of the disclosure provide an erection device that addresses these and other deficiencies of known penis rings.

According to one aspect of the disclosure, the disclosed erection device applies pressure to the shaft of the penis, to the base of the scrotum, or to both, to provide pleasurable sensations to the wearer.

According to another aspect, the erection device restricts the flow of blood out from the penis by compressing a portion of the penis. The restricted blood flow increases the blood pressure within tissues of the penis including the corpus cavernosum and corpus spongiosum, causing the penis to become erect or to increase the tumescence of an erection.

According to another aspect, pressure applied by the erection device to the penis and scrotum delays climax thus increasing the duration of orgasm.

According to another aspect, the erection device provides compression of the dorsal vein of the user's shaft to aid in maintaining an erection during sexual activity.

According to one embodiment of the disclosure, an erection device includes a body designed to be positioned on the wearer's penis near the base of the penis. The disclosed device comprises a body having a latch at one end and having a loop of material connected at the opposite end of the body. The loop is formed from an elastic material. The loop is shaped to be captured in the latch and to be held in the latch when a stretching force is applied to the loop. When the loop is engaged with the latch, the two sides of the loop are separated from one another.

To put the disclosed device on the penis according to one embodiment of the disclosure, the wearer pulls the loop away from the body, stretching the loop. The wearer places the body on the dorsal surface of the penis. The wearer inserts his scrotum and testicles through the loop so that a first portion of the loop is in front of the scrotum and a second portion of the loop is behind the scrotum. The first portion of the loop extends around the penis near the base of the penis. The wearer engages the loop with the latch. The elastic resilience of the loop pulls the loop into the latch, securely engaging the body of the device with the top of the penis and engaging the first portion of the loop around the base of the penis.

Because the device is secured both in front of and behind the scrotum, the device does not rotate around the penis. Thus, the position of the device, and of the body portion of the device are substantially fixed relative to the wearer's anatomy.

According to another embodiment, the loop is slidable through the latch. By sliding the loop, the wearer adjusts the lengths of the first and second portions of the loop. This changes the amounts of pressure the first and second portions of the loop apply to the penis and scrotum, respectively.

According to another embodiment, the body of the device includes one or more structures or mechanisms to enhance sexual pleasure of the wearer or the wearer's sexual partner. Such structures may include textured surfaces adapted to contact and stimulate erogenous tissues, for example, labia, clitoris, anus, and the like or vibrators, mechanical actuators, and the like to apply mechanical energy to erogenous tissues. Because the position of the erection device is substantially fixed relative to the wearer's anatomy, the position and orientation of the structures and devices are likewise fixed. This allows the structures and devices to be properly positioned to induce pleasurable sensations during sexual intercourse.

According to another embodiment, the loop and latch are asymmetrical. The latch is positioned at an opposite end of the body of the device from the loop. This asymmetrical latch-and-loop design makes it easy to get on and off around sensitive anatomy.

According to another embodiment, the latch is formed as a hook with an opening facing upward when the body is placed along the dorsal surface of the penis. This hook is sized so that a portion of the loop fits into the hook when the loop is stretched around the penis and scrotum. Resilient forces on the loop pull the loop into the hook, reliably holding the loop in the hook. According to another embodiment, the latch is formed as a small, elastic catchment and the loop includes a ratchet surface with an insertion tip. The loop is engaged with the latch by inserting the insertion tip though the catchment so that the catchment engages with a selected rib of the ratchet.

According to another embodiment, the latch and loop are formed from materials that allow the loop to slide within the latch. By sliding the loop relative to the latch, the lengths of the first and second portions of the loop in front of and behind, respectively, the wearer's scrotum can be adjusted to adjust the elastic force applied.

According to yet another embodiment, the body of the appliance is formed from two or more layers of material, where each layer has different mechanical properties. According to one embodiment, the body of the device is formed from two layers. An inner layer has a relatively high stiffness, allowing the body to maintain its shape and to apply a firm pressure to the dorsal vein of the penis. An outer layer surrounds the body and is formed from a supple material or a soft elastomer, for example, silicone, that provides a comfortable sensation against the wearer's skin.

According to yet another embodiment, the loop is formed from two or more layers of material. According to one embodiment, the loop has a relatively stiff inner core that provides a selected modulus of elasticity so that sufficient force is applied to the wearer's penis and scrotum. The loop has a softer, more supple, lower elastic modulus outer layer in contact with the wearer's skin.

According to yet another embodiment, the body of the device and/or the loop are formed from materials that can be stretched and that rebound to provide a compressive force, such as an elastomer. Such materials include, but are not limited to one or more of an elastomer a rubber, silicone, natural latex, and synthetic latex.

According to another embodiment, the device is formed from two or more materials that are molded together using one or more molding technique including, but not limited to co-injection molding, insert molding, double shot molding, and over-molding.

According to another embodiment, the outer layer has a lubricious outer surface. The lubricious surface allows the loop to be moved against the wearer's skin when the device is put on and when it is adjusted, for example, by sliding the loop through the latch to balance the force applied by the first and second portions of the loop.

BRIEF DESCRIPTION OF THE DRAWINGS

The above and/or other aspects of the disclosure will be more apparent by describing in detail exemplary embodiments of the disclosure with reference to the accompanying drawings, in which.

DETAILED DESCRIPTION OF EXEMPLARY EMBODIMENTS

Figure 1:
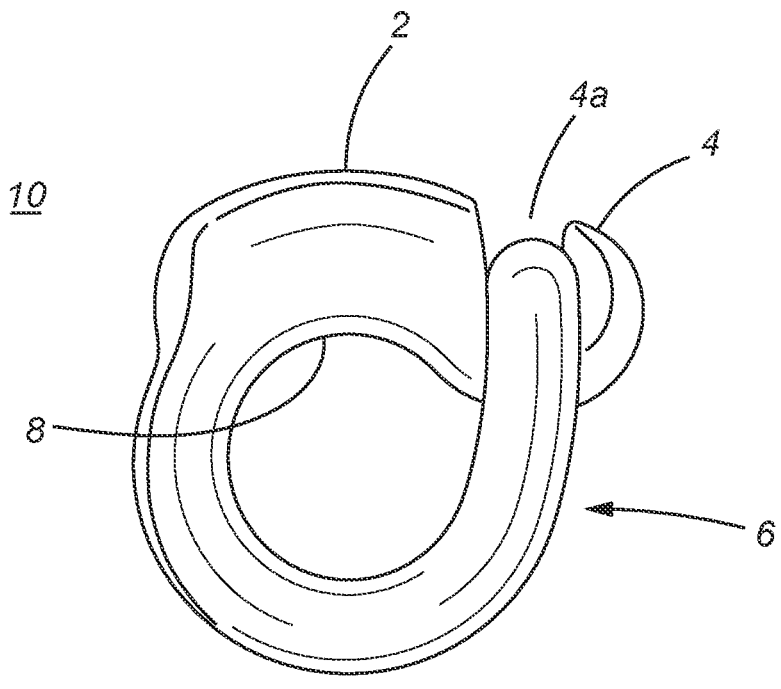
FIG. 1 is a front view of an erection device in a latched configuration according to an embodiment of the disclosure.

Exemplary embodiments of the disclosure will now be described below by reference to the attached Figures. The described exemplary embodiments are intended to assist the understanding of the invention and are not intended to limit the scope of the invention in any way. Like reference numerals refer to like elements throughout.

Figure 2:
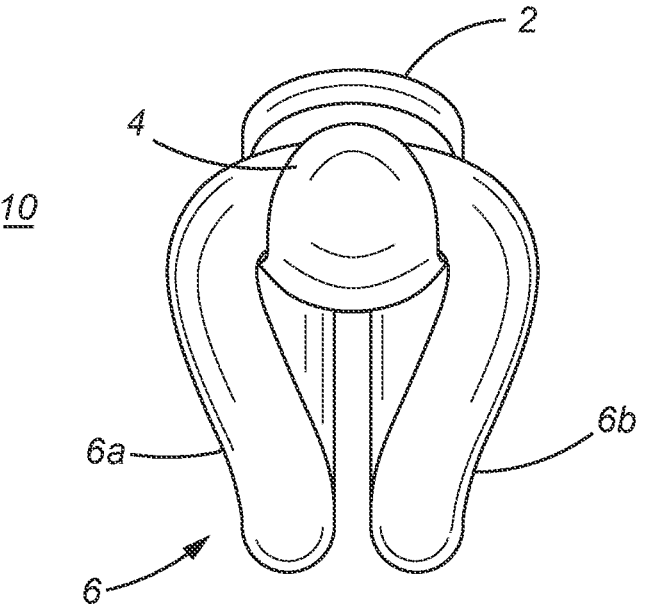
FIG. 2 is a side view of the device of FIG. 1.
Figure 3:
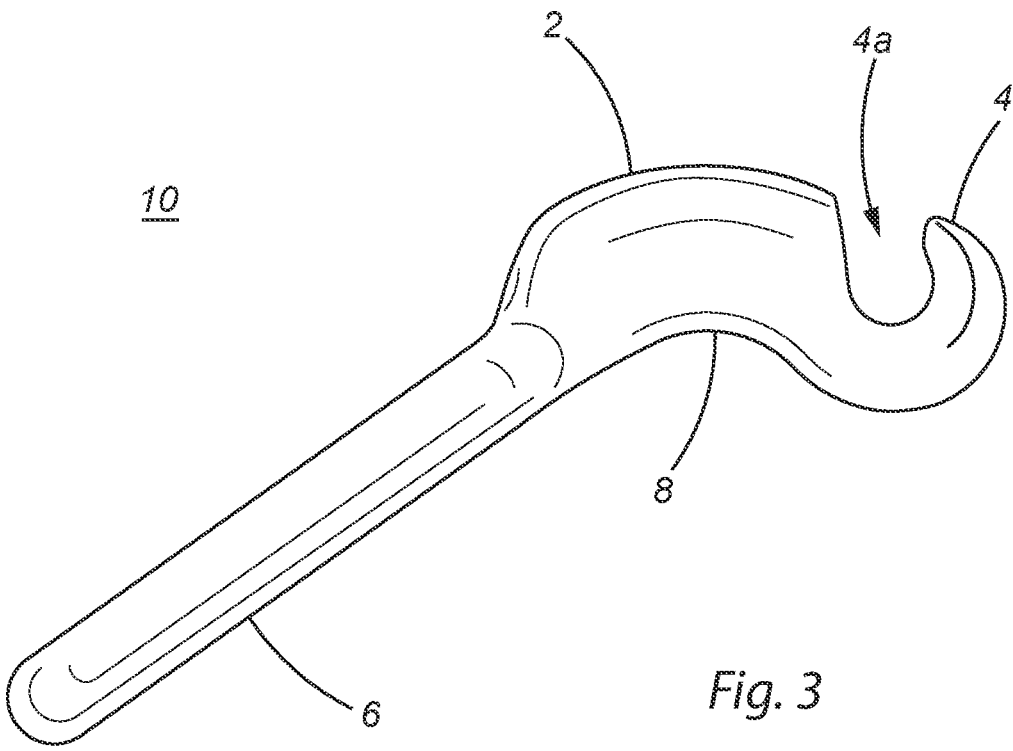
FIG. 3 is a front view of the device of FIG. 1 in an unlatched configuration.
Figure 4:
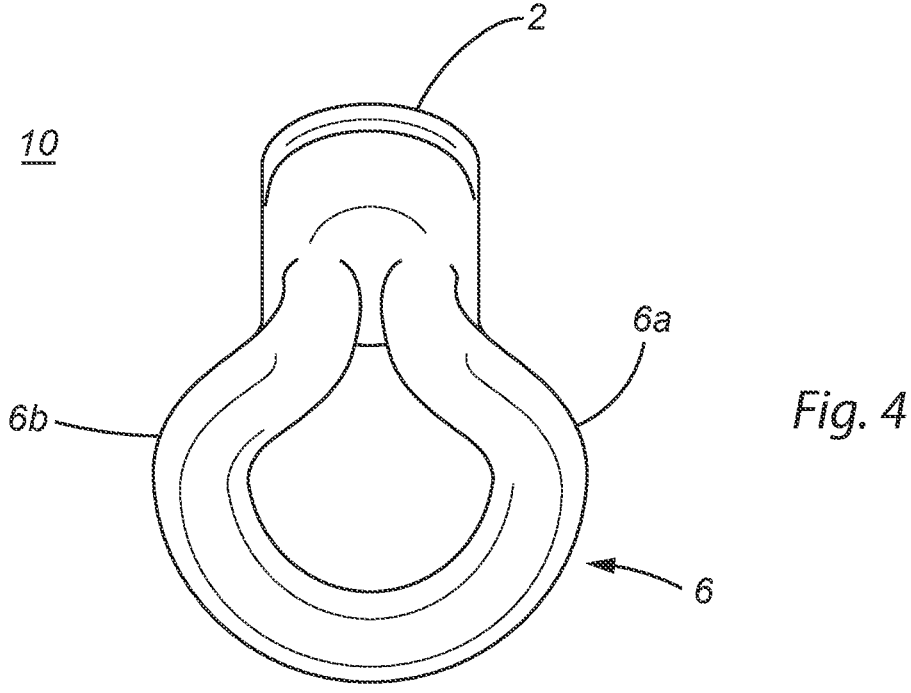
FIG. 4 is a side view of the device of FIG. 1 in the unlatched configuration.
Figure 5A:
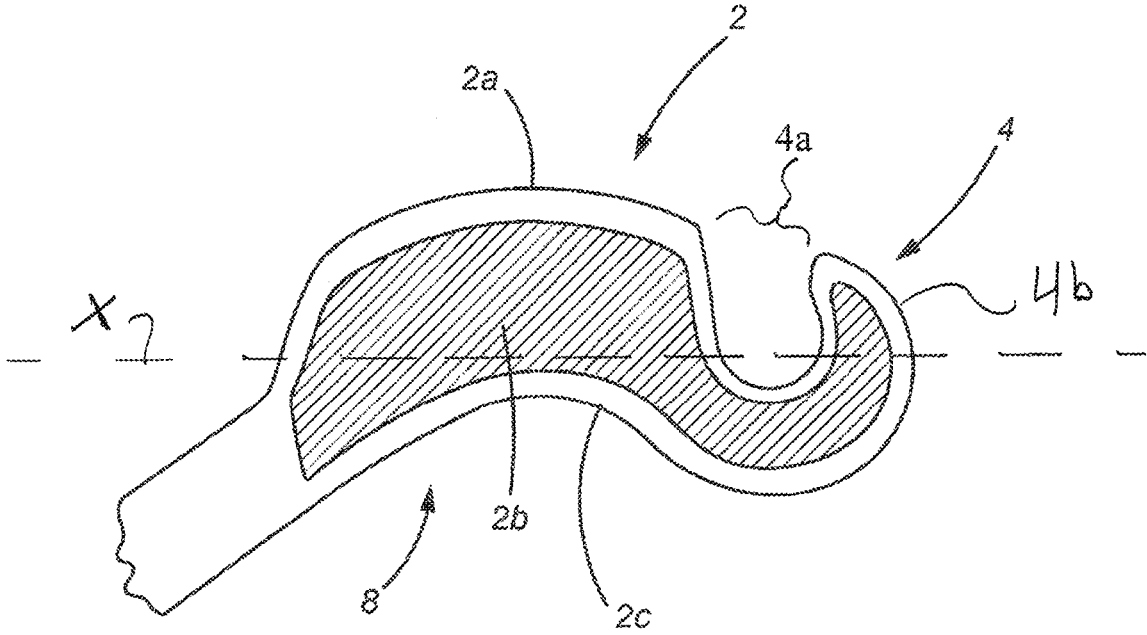
FIG. 5A is a cross section view of an erection device according to a further embodiment of the disclosure.

FIGS. 1 to 4 show an erection device 10 according to one embodiment of the disclosure. In this exemplary embodiment, the device includes a body 2. A contact surface 8 of body 2 is curved to conform with the dorsal surface of a human penis. At one end of the body is a latch 4. Body 2 extends in a longitudinal direction along longitudinal axis X, as shown in FIG. 5A. Loop 6 is connected at the opposite end of the body from latch 4 along longitudinal axis X. Latch 4 is shaped to allow loop 6 to be captured and securely held, as shown in FIGS. 1 and 2. As shown in FIG. 5A, latch 4 consists of hook 4b with an opening 4a. Opening 4a extends in direction transverse to longitudinal axis X. According to one embodiment, opening 4a extends perpendicular to the longitudinal axis. Opening 4a is sized to allow at least a portion of the loop to engage with the hook. Loop 6 extends through opening 4a in the transverse direction. FIGS. 3 and 4 show the loop 6 disengaged from latch 4. As shown in FIG. 2, when loop 6 is engaged with latch 4, two portions 6a, 6b of the loop are defined.

Loop 6 shown in FIGS. 1-4 has a round cross section and has the same diameter along the length of the loop. The disclosure is not limited to a loop with such a shape. According to other embodiments, loop 6 has a rectangular, oval, square, triangular or other cross-sectional shape. According to other embodiments, the cross section of loop 6 varies along its length, for example, to provide a larger or smaller cross section along portions of the loop that will engage with selected parts of a wearer's anatomy when the device is worn.

FIG. 5A shows a cross section of body 2. According to one embodiment, body 2 includes a relatively rigid core structure 2b. Latch 4 is formed by substantially rigid structure 2b, providing a secure structure to capture and hold the loop that resists deformation when stretching forces are applied to the loop. Outer layer 2a surrounds structure 2b to form the surface of body 2. Outer layer 2a may be formed from a relatively soft material that can comfortably contact the wearer's skin. According to one embodiment, core 2b is formed from a plastic, a metal, or a ceramic.

According to one embodiment, a skin contact layer 2c is provided on curved contact surface 8. Skin contact layer 2c may be formed from the same material as outer layer 2a or may be formed from a different material, for example, to provide a selected friction between body 2 and the wearer's skin.

Loop 6 is formed from an elastic material with a selected modulus. According to one embodiment, loop 2 is formed from the same material as outer layer 2a of body 2 so that the outer surface of the whole device 10 is a continuous surface. According to one embodiment, the material forming outer layer 2a and loop 6 has lubricious surface that facilitates sliding device 10 along the wearer's skin to reduce discomfort if the device is repositioned when it is worn. The material forming the loop is selected to have a hardness measured on the Shore OO scale between about 0030 and 0050. According to a preferred embodiment, the loop is formed from a material with a hardness of about 0040.

The material or materials forming device 10 are preferably polymers. According to one embodiment, portions of device 10 are formed from one or more of natural rubber, polyisoprene, butyl rubber, chloroprene, ethylene propylene diene, a fluorocarbon, a fluorosilicone, nitrile rubber, silicon rubber, styrene-butadiene rubber, polyurethane, and the like.

Figure 5B:
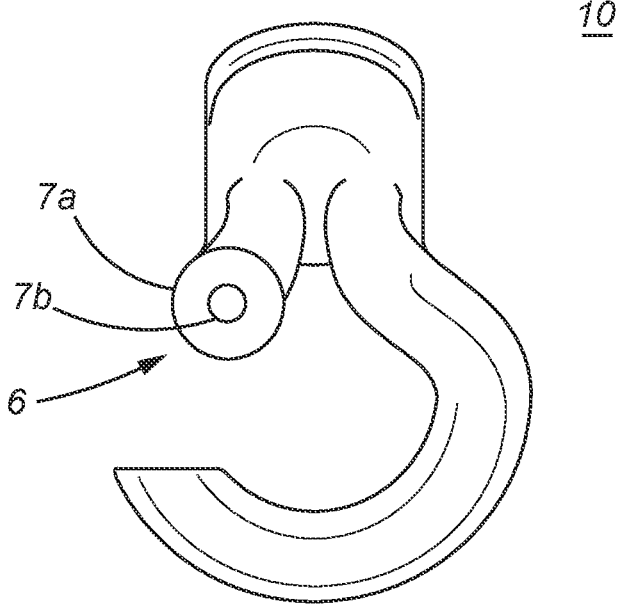
FIG. 5B is a cross section view of the loop of an erection device according to another embodiment of the disclosure.

FIG. 5B shows a partial cross section of loop 6 according to another embodiment. Outer layer 7a of loop 6 is formed from a material suitable for contact with the skin of the wearer. As discussed above, such a material may be selected to provide a soft, supple surface to comfortable contact the wearer's skin. Loop 6 includes a central core 7b. Core 7b is made from a material that has a selected modulus of elasticity to provide a suitable force to the tissues of the penis and scrotum when the device is worn. Core 7b may be formed from a different material than the outer layer 7a. According to one embodiment, core 7b is formed from a metallic spring, such as a coil spring. According to one embodiment, core 7b connects with rigid core 2b of body 2.

According to one embodiment, one or more of the body 2, loop 6, and outer layer 2a are formed by injection molding. According to one embodiment, body 2 is first formed by a known technique, such as injection molding to create a solid object. The formed body 2 is positioned in a mold cavity shaped to form the outer layer 2a and loop 6. The mold cavity is closed around body 2 and the material forming outer layer 2a and loop 6 are injected into the mold cavity to form device 10.

Figure 6:
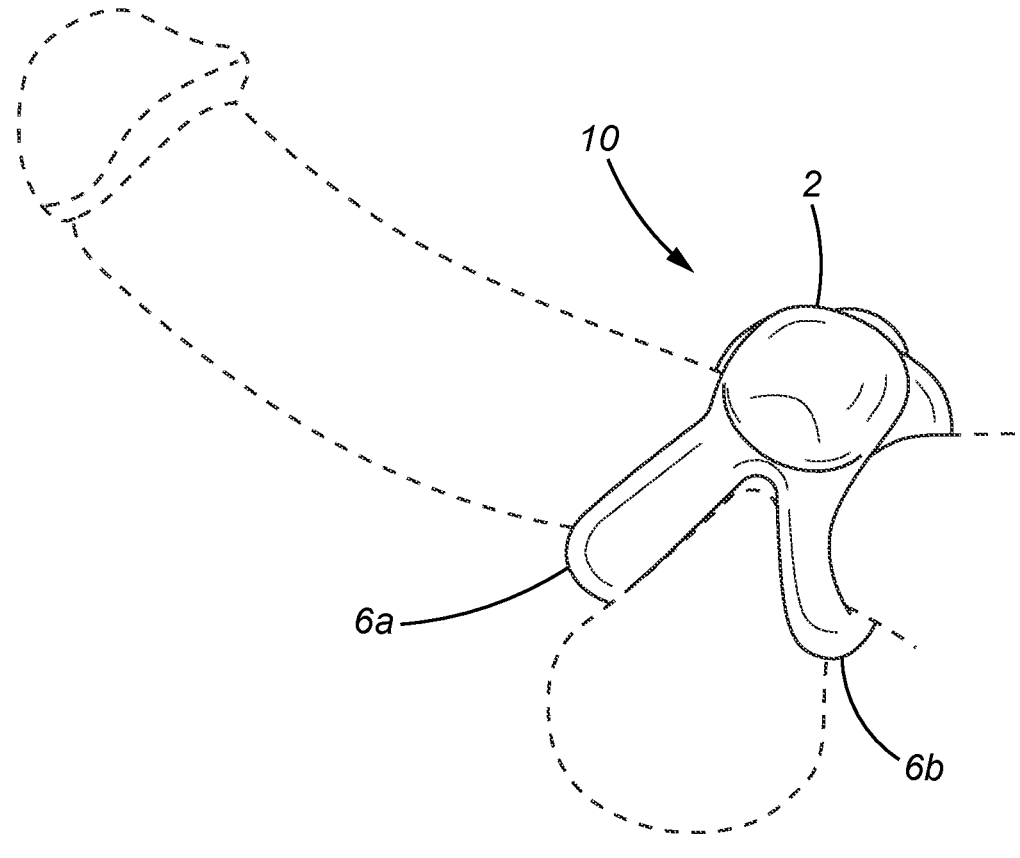
FIG. 6 is a side view of a device according to an embodiment of the disclosure attached to the penis and scrotum of a human male.
Figure 7A:
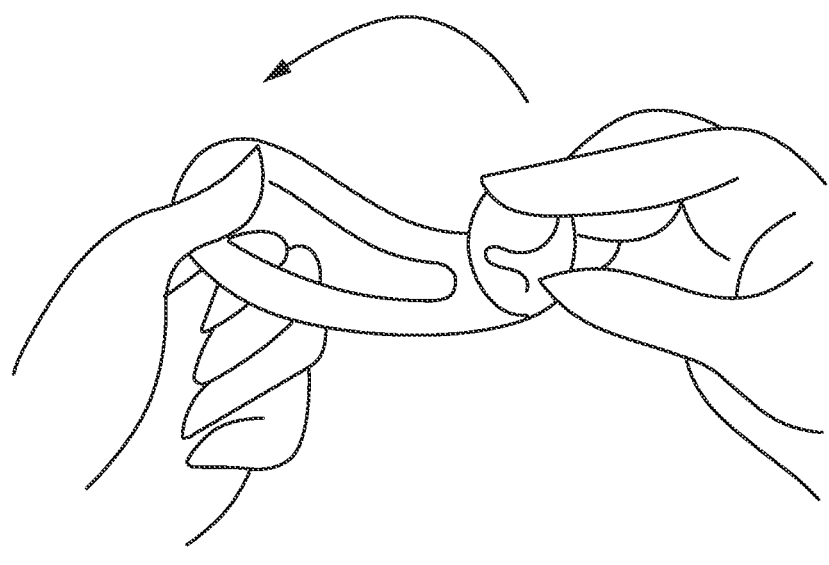
FIGS. 7A-7C illustrate steps for attaching an erection device to a penis and scrotum according to embodiments of the disclosure.
Figure 7B:
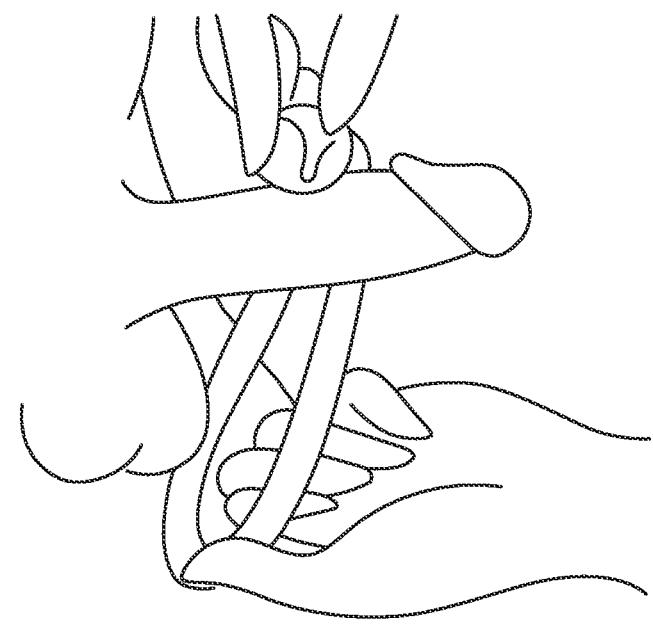
Figure 7C:
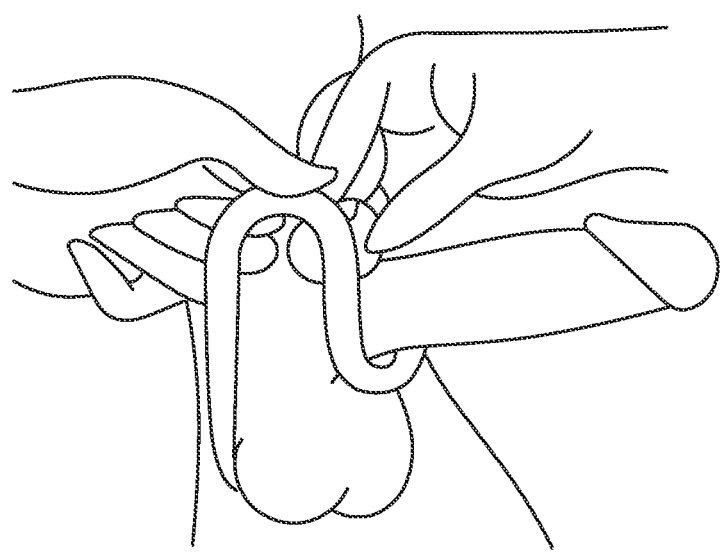

FIG. 6 shows the device 10 attached to the penis of a wearer. FIGS. 7A-7C illustrate the steps to attach the device. As shown in FIG. 7A, the wearer holds body 2 in one hand and stretches loop 6 away from body 2. As shown in FIG. 7B, the wearer places body 2 on the dorsal surface of his penis and inserts his scrotum and testicles through loop 6. One portion 6a of loop 6 is positioned in front of the scrotum and another portion 6b is positioned behind the scrotum. As shown in FIG. 7C, the wearer engages the loop 6 with latch 4. Elastic resilience of loop 6 pulls the loop into the latch, securing the device onto the penis and applying compressive force to the penis and scrotum. Loop 6 is sized to allow it to slide through latch 4. This allows the wearer to pull on either portion 6a or 6b to adjust the length of these two portions to adjust the amount of elastic force applied to the penis and scrotum. To remove the device, the wearer disengages loop 6 from latch 4.

Figure 8:
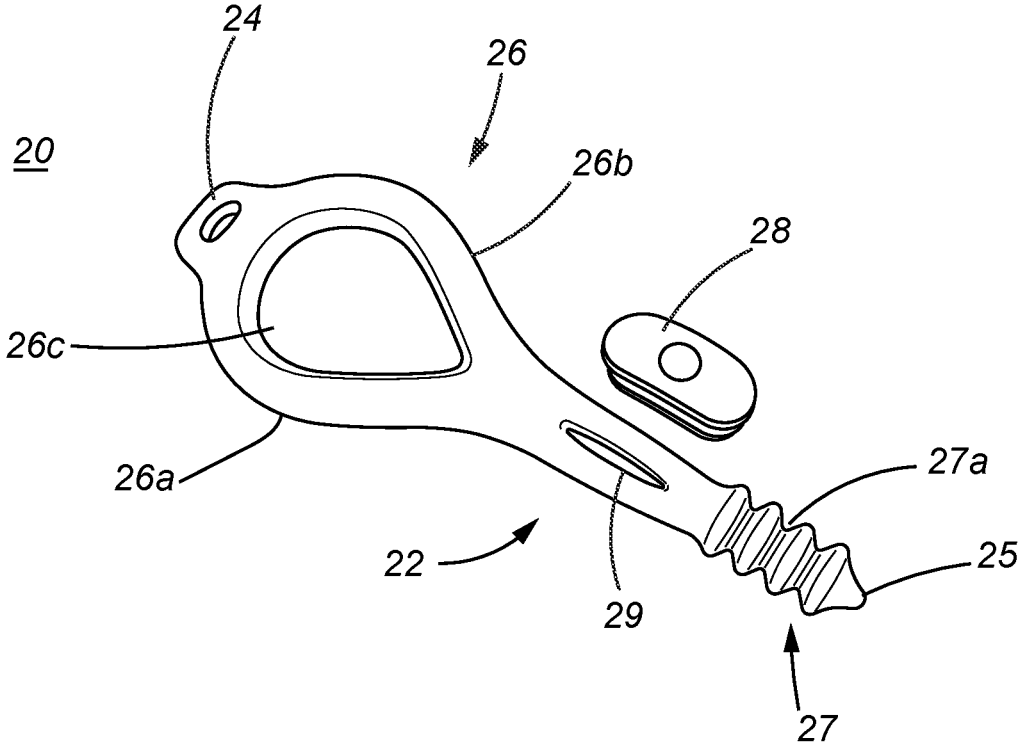
FIG. 8 is a perspective view of an erection device according to a further embodiment of the disclosure.

FIG. 8 shows another embodiment of the disclosure. Device 20 is formed from a loop part 26 and a body part 22. Catchment 24 is provided at one side of loop part 26. Body part 22 is connected with the other side of loop part 26. Ratchet 27 is provided at the side of body part 22 opposite from loop part 26. Ratchet 27 has one or more notches 27a. An insertion tip 25 is provided at the side of ratchet 26 opposite from body part 22.

As with the prior embodiments, loop part 26 is formed by first and second loop portions 26a and 26b. Loop opening 26c is formed between the loop portions 26a, 26b. As with previous embodiments, device 20 is formed from an elastic material that can be stretched when the device is attached and that provides a force on the wearer's penis due to the elastic rebound of the device once attached.

According to one embodiment, device 20 is attached to the wearer's penis and testicles by positioning body part 22 against the dorsal surface of the penis. Loop part 26 is pulled away from body part 22 and the wearer inserts his testicles through loop open 26c so that first loop part 26a is positioned in front of the scrotum and second loop part 26b is positioned behind the scrotum. The wearer inserts insertion tip 25 of ratchet 27 into catchment 24. Catchment 24 stretches to accept ratchet 27 and engages with a selected notch 27a on the ratchet to fix the device 20 to the wearer's penis and scrotum. The device can be tightened or loosened by moving catchment 24 to a different selected notch 27a of ratchet 27.

According to one embodiment, body part 22 includes slot 29. Accessory 28 is shaped to be inserted into slot 29 to removably attach the accessory 28 to device 20. According to one embodiment, accessory 28 includes a structure or device, such as a vibrator, a tickler, or other apparatus to engage with and/or stimulate sensitive anatomical regions of the wearer and/or the wearer's sexual partner.

While the invention has been particularly shown and described with reference to exemplary embodiments thereof, the invention is not limited to these embodiments. It will be understood by those of ordinary skill in the art that various changes in form and details may be made therein without departing from the spirit and scope of the invention as defined by the following claims. Therefore, the description should not be construed as limiting the scope of the invention.

What is claimed is:

1. An erection device comprising:
   a latch;
   a loop having two loop ends and forming a loop opening; and
   a body, wherein the latch is provided on a first end of the body, wherein the two loop ends are connected with a second end of the body opposite from the first end, wherein the first and second ends are arranged along a longitudinal axis, wherein the body has a concave surface extending from the first end to the second end, wherein the latch comprises a hook, wherein the hook has a hook opening extending in a transverse direction to the longitudinal axis, wherein the loop is formed from an elastic material, wherein, when the loop is engaged with the latch the loop extends in the transverse direction through the opening, wherein the loop defines a first loop portion and a second loop portion, wherein the first loop portion is adapted to extend around a shaft of a penis of a wearer and the second loop portion is adapted to extend around the penis and a scrotum of the wearer, and wherein the concave surface is adapted to contact a dorsal surface of the penis.

2. The device of claim 1, wherein the transverse direction is perpendicular to the longitudinal axis.

3. The device of claim 1, wherein the latch and loop are sized to allow the loop to slide through the latch to adjust the relative lengths of the first portion and second portion.

4. The device of claim 1, wherein the body further comprises an inner core having a first hardness and an outer layer having a second hardness, wherein the first hardness is greater than the second hardness, and wherein at least a portion of the latch is formed by the inner core.

5. The device of claim 4, wherein one or more of the loop and the outer layer are formed from an elastic material.

6. The device of claim 5, wherein the elastic material is one or more of an elastomer, a rubber, silicone, natural latex, synthetic latex, polyisoprene, butyl rubber, chloroprene, ethylene propylene diene, a fluorocarbon, a fluorosilicone, nitrile rubber, silicon rubber, styrene-butadiene rubber, and polyurethane.

7. The device of claim 5, wherein the loop is continuous with and formed from the same material as the outer layer.

8. The device of claim 1, wherein one or more of the body and the loop further comprise a lubricious outer surface.

9. A method of enhancing an erection of a wearer comprising the steps of:

providing a latch;

providing an elastic loop having two loop ends and forming a loop opening, wherein the latch comprises a hook with a hook opening sized to allow the loop to engage with the hook;

providing a body, wherein the latch is provided on a first end of the body, wherein the two loop ends are connected with a second end of the body opposite from the first end, wherein the first and second ends are arranged along a longitudinal axis, wherein the hook opening extends in a transverse direction to the longitudinal axis, wherein the loop is formed from an elastic material;

placing the body on a dorsal surface of a penis of the wearer when the loop is disengaged from the latch, wherein the hook opening faces away from the dorsal surface of the penis;

stretching the loop away from the body;

inserting a scrotum of the wearer through the loop; and after the step of inserting, engaging the loop with the hook by inserting the loop into the opening, wherein the loop extends in the transverse direction through the opening, wherein the loop defines a first loop portion and a second loop portion, and wherein the first loop portion extends around the shaft of the penis and the second loop portion extends around the penis and a scrotum, wherein rebound of the elastic loop applies a compressive force to the penis or the scrotum.

10. The method of claim 9, further comprising the step of, after engaging the loop with the latch:

sliding the loop in the transverse direction relative to the hook opening, wherein lengths of the first and second loop portions of the loop are varied.

11. The method of claim 9, wherein the transverse direction is perpendicular to the longitudinal axis.

\* \* \* \* \*